United States Patent [19]

Kaster

[11] 4,306,319
[45] Dec. 22, 1981

[54] HEART VALVE WITH NON-CIRCULAR BODY

[75] Inventor: Robert L. Kaster, 2730 Vagabond La., Plymouth, Minn. 55447

[73] Assignee: Robert L. Kaster, Plymouth, Minn.

[21] Appl. No.: 160,047

[22] Filed: Jun. 16, 1980

[51] Int. Cl.³ .............................................. A61F 1/22
[52] U.S. Cl. ........................................ 3/1.5; 137/527; 137/527.8
[58] Field of Search ................... 3/1.5; 137/527, 527.8

[56] References Cited

U.S. PATENT DOCUMENTS

| | | | |
|---|---|---|---|
| 3,438,394 | 4/1969 | Nakib | 3/1.5 X |
| 3,451,067 | 6/1969 | Jordan | 3/1.5 |
| 3,476,143 | 11/1969 | Kaster | 3/1.5 X |
| 3,538,514 | 11/1970 | Schimert et al. | 3/1.5 |
| 3,725,961 | 4/1973 | Magovern et al. | 3/1.5 |
| 3,737,919 | 6/1973 | Child | 3/1.5 |
| 3,739,402 | 6/1973 | Cooley et al. | 3/1.5 |
| 3,824,629 | 7/1974 | Shiley | 3/1.5 |
| 3,825,957 | 7/1974 | Kaster | 3/1.5 |
| 3,835,475 | 9/1974 | Child | 3/1.5 |
| 3,903,548 | 9/1975 | Nakib | 3/1.5 |
| 3,926,215 | 12/1975 | Macleod | 3/1.5 X |
| 4,021,863 | 10/1977 | Woien | 3/1.5 |
| 4,057,857 | 11/1977 | Fettel | 3/1.5 |
| 4,078,268 | 3/1978 | Possis | 3/1.5 |
| 4,114,202 | 9/1978 | Roy et al. | 3/1.5 |
| 4,159,543 | 7/1979 | Carpentier | 3/1.5 |
| 4,178,639 | 12/1979 | Bokros | 3/1.5 |
| 4,197,593 | 4/1980 | Kaster et al. | 3/1.5 |
| 4,204,283 | 5/1980 | Bellhouse et al. | 3/1.5 |
| 4,225,980 | 10/1980 | Martinez | 3/1.5 |

FOREIGN PATENT DOCUMENTS 2007333  5/1979  United Kingdom ................. 3/1.5

Primary Examiner—Ronald L. Frinks
Attorney, Agent, or Firm—Joseph F. Breimayer; Carl A. Forest

[57] ABSTRACT

Heart valve including a valve body having a non-circular exterior periphery and a blood flow passage orifice through the valve body having a periphery substantially geometrically similar to the exterior periphery. A rigid occluder having a periphery slightly smaller than the internal periphery of the blood flow passage, pivots within the confines of the blood flow passage. The valve body can assume an oval, egg, kidney, or the like geometrical shape and pivots on an axis parallel or removed from the major axis of the non-circular heart valve body. The occluder pivots about pivot closed pivots and pivot open pivots, guide struts, or a T-shaped pivot post between occluding and non-occluding positions. Stop surfaces all retain the occluder in the occluding position and non-occluding position in the heart valve orifice.

20 Claims, 20 Drawing Figures

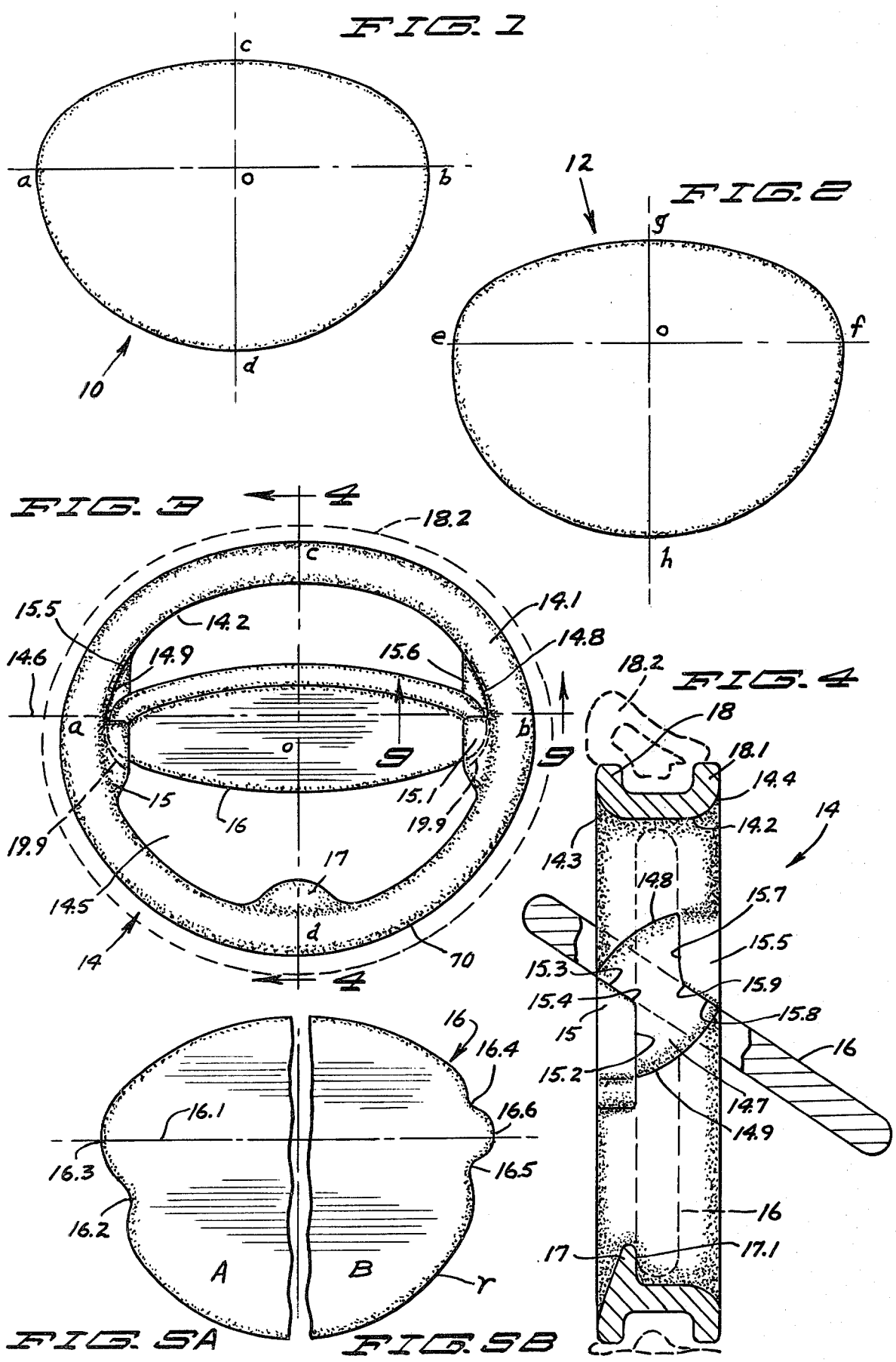

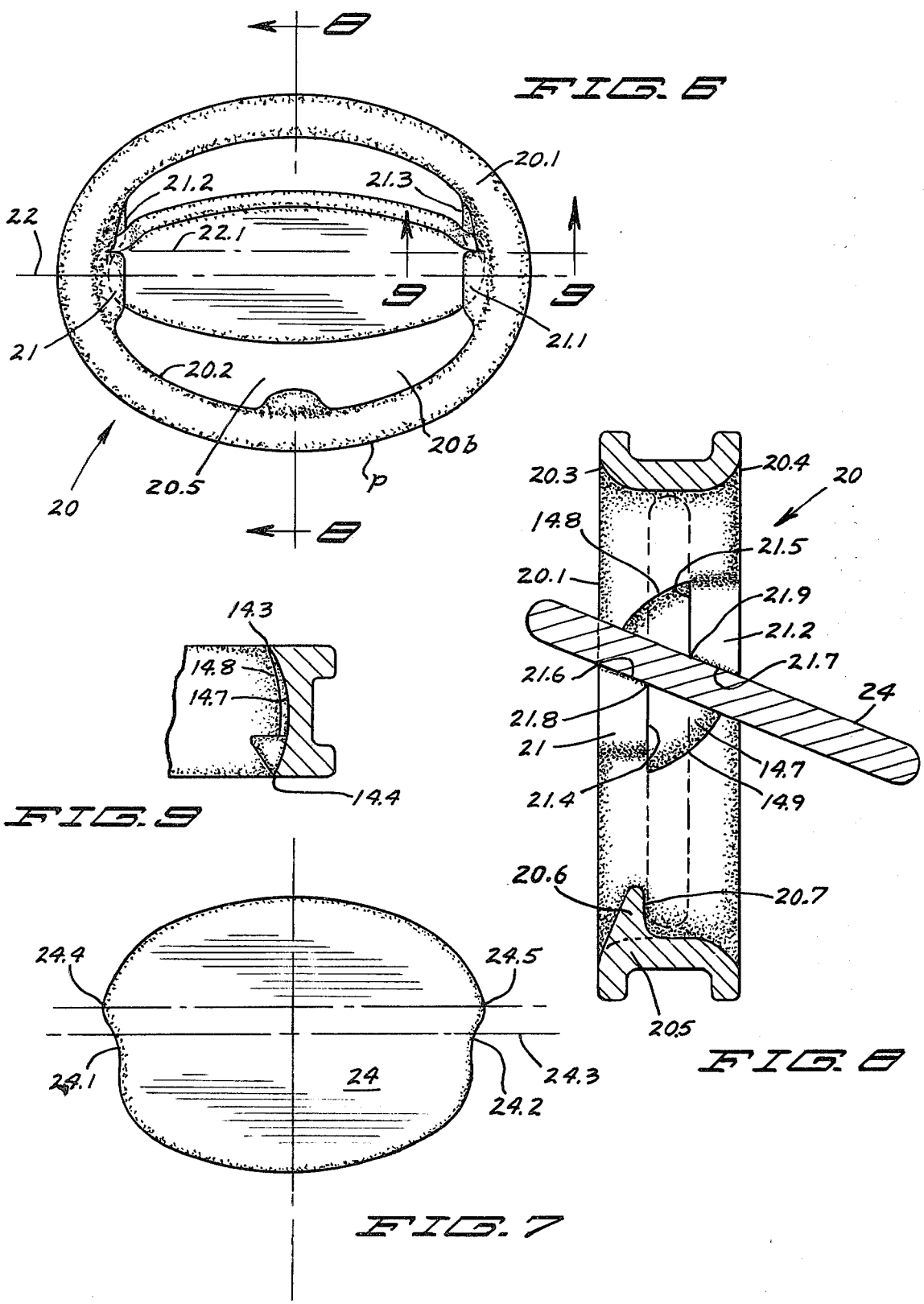

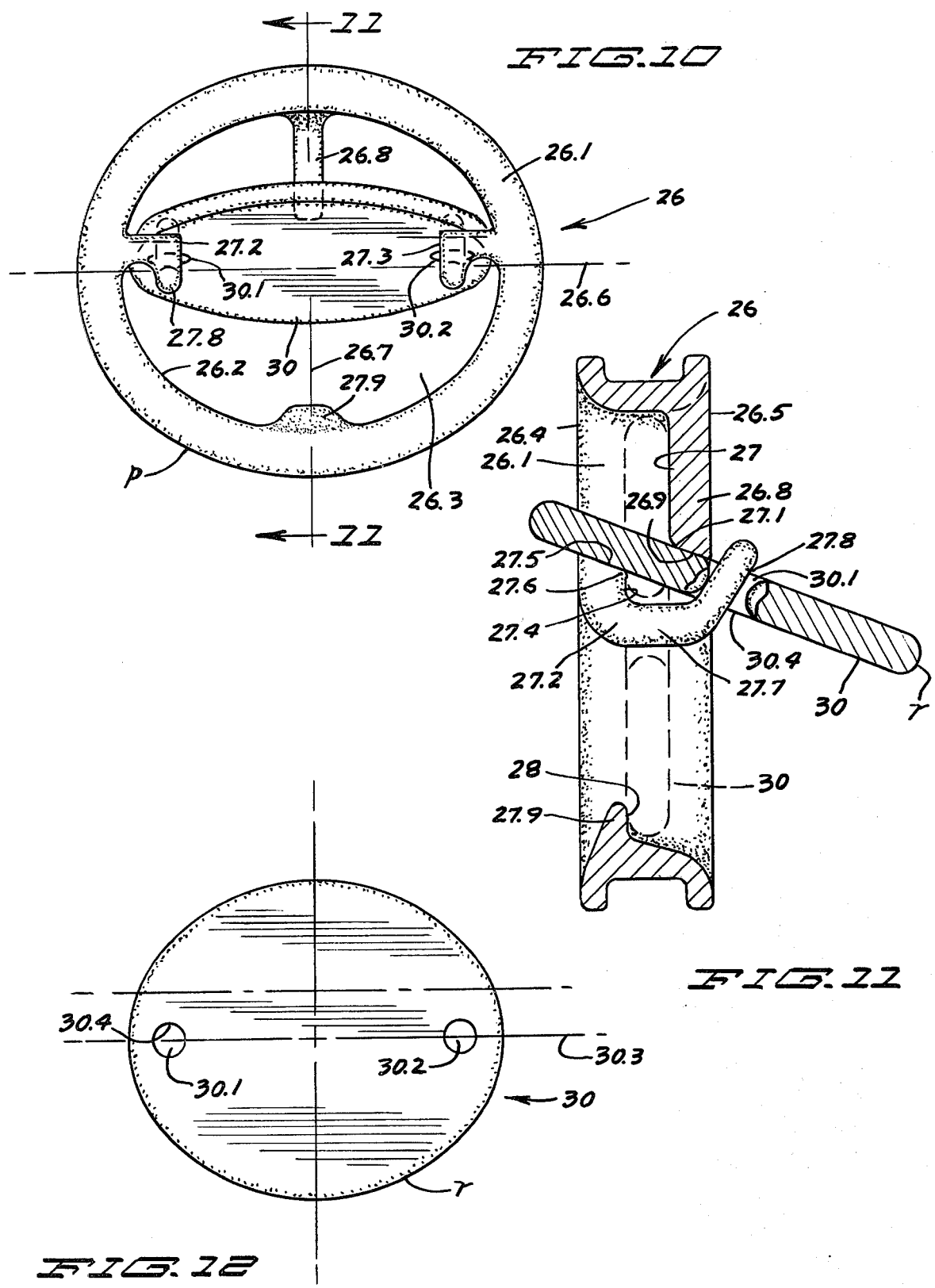

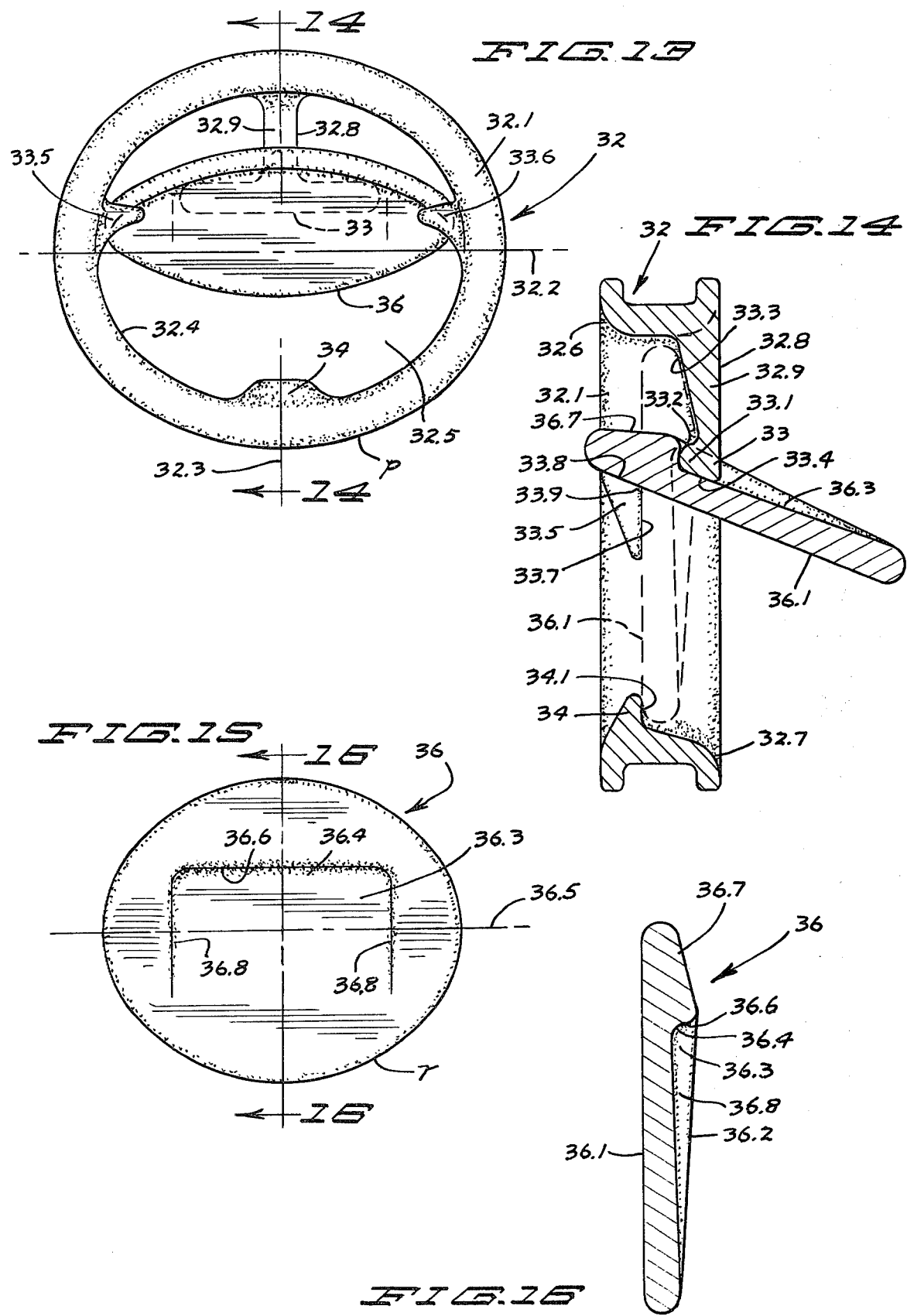

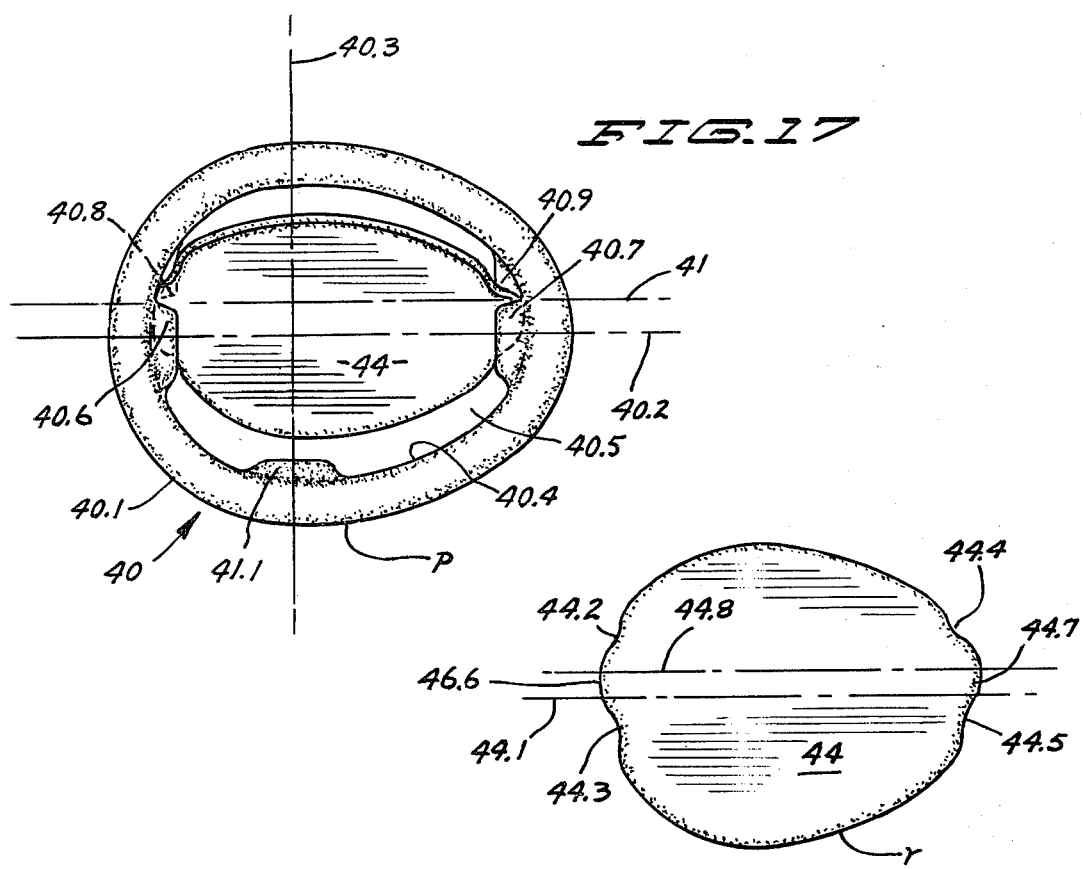
FIG. 17
FIG. 18
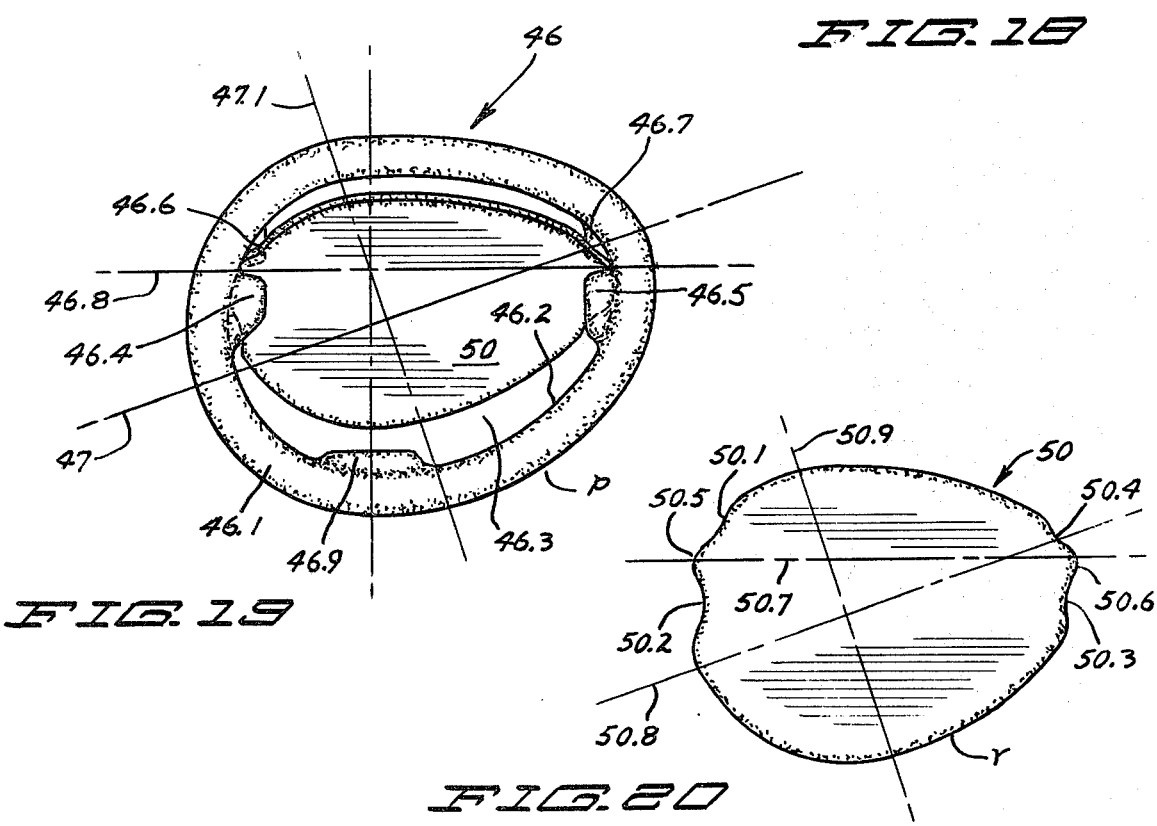
FIG. 19
FIG. 20

HEART VALVE WITH NON-CIRCULAR BODY

BACKGROUND OF THE INVENTION

1. Field of the Invention

The present invention relates generally to artificial body members, and more specifically, pertains to a pivoting disc heart valve having a non-circular valve body.

2. Description of the Prior Art

Diseased or damaged heart valves are now surgically replaced with artificial heart valves. With certain artificial valves, attempts have been made to duplicate the action of natural valves. At least one such valve has employed actual human tissue (fascia lata) in a graft technique as set forth by Cooley et al in U.S. Pat. No. 3,739,402. Mechanical heart valves, that is, valves employing rigid occluders moveable physically or pivotally or both between occluding and nonoccluding positions, are generally preferred by surgeons and have largely replaced other artificial valves. The use of pre-manufactured mechanical heart valves shortens the time required for surgery since there is no need for the surgeon to fashion a valve from human tissue to the correct size and shape during surgery. Moreover, the use of mechanical valves avoids sterility problems since the valves can be pre-sterilized. Also, no coincident or prior surgery is necessary to obtain graft tissue from the patient such as fascia lata. Finally, mechanical valves are pretested for operability, and are furnished in a variety of sizes so that the correct valve is immediately available to the surgeon for implantation during valve replacement surgery.

Mechanical heart valves ordinarily are provided with a circular valve body about which is affixed a circular sewing, or suture, ring. The natural heart orifice is first prepared for reception of the mechanical valve by surgical removal of diseased or damaged heart valve tissue and adjacent tissue that may interfere with the proper operation of the mechanical valve. During implantation, the suture ring is sewn to the natural heart tissue orifice to achieve fixation of the mechanical valve.

The circular peripheral configuration of prior mechanical heart valves is an extrapolation for using valve occluders having circular cross-sections in planes normal to the direction of blood flow. For example, the heart valve commonly known as the Smeloff-Cutter valve employs a spherical occluder in a wire basket or cage. Other valves have employed toroidal occluders, and one such valve is illustrated in U.S. Pat. No. 3,438,394. Other valves, such as the Cooley-Cutter valve, have employed disc occluders of circular cross-section. One such valve is illustrated in U.S. Pat. No. 3,725,961. Other valves, exemplified by the Lillihei-Kaster valve, have employed circular disc occluders pivotable between open and closed positions within an annular valve body. One such valve is illustrated in U.S. Pat. No. 4,021,863.

Although the orifices of the aortic and pulmonary valves in the human heart are predominently circular, the orifices of the mitral and tricuspid valves are rather elongated or oval in shape. The circular peripheries of the above-described mechanical heart valves generally match the predominently circular orifices of the aortic and pulmonary natural heart valves. As a result, the peripheral tissues of aortic and pulmonary valves are not unduly distorted when mechanical valves with circular peripheries are implanted therein. However, the implantation of a mechanical heart valve having a circular periphery into the oval shaped orifice of a mitral or tricuspid valve requires the natural orifice tissues to become distorted into a circular configuration thereby not only causing stress of the tissue comprising the natural valve orifice but also on the sutures or stitches that are employed to hold the mechanical valve in place. The permanent distortion of the peripheral natural valve orifice tissue from the normal oval configuration to the forced circular configuration does not produce any beneficial effect and the stresses produced by such distortion are best avoided.

The heart valve of the present invention is particularly characterized in having an oval exterior valve body periphery which closely conforms to the oval configuration of the natural heart valve orifice.

SUMMARY OF THE INVENTION

The present invention provides a heart valve including a non-circular valve body having a blood flow passage and a rigid occluding disc for regulating the flow of blood through the blood flow passage. The occluding disc moves between a closed occluding position and an open non-occluding position in the blood flow passage. The periphery of the occluder is substantially geometrically similar to the geometric shape of the blood flow passage. The valve body is provided with an oval exterior periphery for attachment to an oval natural heart valve tissue orifice. Oval refers to a closed curve which is not circular and is not used in a limiting sense. An oval curve is characterized by having significantly different maximum dimensions at right angles to each other where one of the maximum dimensions is the longest dimension across the curve. Oval geometric curves include ellipses, egg-shaped oval curves, kidney-shaped curves, and other similar geometric figures. The oval shapes described herein lie in a plane and are substantially inwardly concave about the periphery. The ratio of the smaller to the larger maximum dimension across the periphery is in the range of 0.4 to 0.9 by way of example and for purposes of illustration only. The heart valve is attached to the tissue of the heart valve orifice by a pliable sewing ring contoured to the periphery of the oval valve body.

According to one embodiment of the present invention, there is provided an oval heart valve including an annular valve body having an exterior periphery in that the periphery comprises sections of two elliptical curves having at least one common major axis, an inner wall diverging outwardly forming inflow and outflow sides and defining a periphery of a blood flow passage orifice through the valve body, the periphery geometrically corresponding to the exterior periphery, opposing pivots projecting into the orifice adjacent to the major axis and each of the pivot sockets including an arcurate ridge on an inwardly concave portion, a pivot closed pivot having an open position stop surface, a pivot edge, and a closed position stop surface, a pivot open pivot having an open position stop surface, a pivot edge and a closed position stop surface, a thin rigid disc occluder having an oval periphery slightly smaller than the internal periphery of the orifice and including notches about a sharply rounded portion on the edge of the disc at each end of the major axis of the disc which fit into each of the pivot sockets, a pivot stop having a downstream facing stop surface projecting into the orifice and spaced flanges extending outwardly from the valve body whereby the spatial relationship between the open-position disc stops governs the full-open-position of the disc to the plane of the valve orifice in an open non-occluding position and the closed position supports the occluder in a closed occluding position. The notches can be either a single concave notch about a sharply rounded periphery of the disc or a double concave notch.

According to another embodiment of the present invention, there is provided an oval heart valve similar in structure to the first embodiment, but having an occluding disc which pivots on an axis parallel and spaced from the major axis of the occluding disc.

According to a further embodiment of the present invention, there is provided an oval heart valve having an occluding disc which pivots on an axis parallel and removed from the major axis of the occluding disc on opposing disc guide struts.

According to an additional embodiment of the present invention, there is provided an oval heart valve having an occluding disc which pivots on an axis parallel and removed from the major axis of the occluding disc on a T-shaped pivot post about opposed pivot closed projections where a disc pivot socket is located along a pivot axis of the occluding disc. The T-shaped pivot post functions as a pivot-open pivot, an open-position disc stop, and disc retention. The T-shaped pivot post cooperates with the occulating disc to regulate valving.

According to a further additional embodiment of the present embodiment, there is provided an oval heart valve having an egg-shaped periphery.

According to a still additional embodiment of the present embodiment, there is provided an oval-shaped heart valve having a kidney-shaped periphery.

Significant aspects and features are that an oval heart valve with a surgical suturing ring implanted in either the mitral or tricuspid positions produces a better result than a prosthesis with a circular orifice. The oval shaped prosthetic heart valve does not distort the annulus and surrounding tissue. The heart has the ability to contract in a normal fashion and recover its pumping capacity more readily. Finally, an oval-shaped mitral or tricuspid prosthesis enables the heart to function with better hemodynamic efficiencies.

The heart valve having a non-circular body is better suited for implanation in the mitral or tricuspid position of the heart as the annuli of these two natural valves are predominantly oval shaped.

The heart valve is of a low profile structure as the entire structure of the valve is confined to the height of the valve base which is beneficial because of the space limitations within the heart.

The heart valve is quiet in operation in that the edge of the disc contacts the isolated disc stop and travels a shorter accurate distance. The force of the closing impact is minimal and, therefore, the sound generated by the closing impact is less significant.

The disc of this heart valve pivots on a major axis which is within the orifice. In the open position, the edge of the disc slants toward the major axis of the orifice and away from encroachment with the annular tissue.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the FIGURES thereof and wherein:

FIGS. 1 and 2 exemplify different oval curves as defined in the specification herein;

FIG. 3 is a view of an oval heart valve of the present invention taken from the upstream side;

FIG. 4 is a cross-sectional view taken along line 4-4 of FIG. 3;

FIGS. 5A and 5B are cut plan views of an occluder for the valve of FIG. 3 having a 5A side and a 5B side;

FIG. 6 is a view of another embodiment of an oval heart valve of the invention taken from the upstream side;

FIG. 7 is a top view of an occluder for the valve of FIG. 6;

FIG. 8 is a cross-sectional view taken along line 8-8 of FIG. 6;

FIG. 9 is a cross-sectional view taken along line 9—9 of FIG. 6 and also along line 9—9 of FIG. 3;

FIG. 10 is a view of a further embodiment of an oval heart valve of the invention taken from the upstream side;

FIG. 11 is a cross-sectional view taken along line 11—11 of FIG. 10;

FIG. 12 is a plan view of an occluder for the valve of FIG. 10;

FIG. 13 is a view of an additional embodiment of an oval heart valve of the present invention taken from the upstream side;

FIG. 14 is a cross-sectional view taken along line 14—14 of FIG. 13;

FIG. 15 is a plan view of an occluder for the valve of FIG. 13;

FIG. 16 is a cross-sectional view taken along line 16-16 of FIG. 15;

FIG. 17 is a view of a further additional embodiment of the valve of the invention taken from the upstream side; FIG. 18 is a plan view of an occluder for the valve of FIG. 17;

FIG. 19 is a view of a still additional embodiment of the valve of the invention taken from the upstream side; and FIG. 20 is a plan view of an occluder for the valve of FIG. 19.

DESCRIPTION OF THE PREFERRED EMBODIMENTS

FIGS. 1 and 2 illustrate exemplary oval curves 10 and 12. The oval curve 10 of FIG. 1 has a longest dimension along line aob. The maximum dimension across the curve at right angles to line aob is measured along line cod. The curve acb represents one-half of an ellipse having line aob as an axis and having line co as a portion of its minor axis. The part adb of the curve represents a section of an ellipse having the line aob as the major axis and having line od as a portion of the minor axis. The two ellipse portions have line aob as a common major axis. The oval curve 12 of FIG. 2 has a longest dimension alog line eof. The maximum dimension across the curve at right angles to line eof is measured along line goh. The curve egf represents a section of an ellipse having line eof as a major axis and having line og as a portion of its minor axis. The other half of the curve ehf, however, is a semicircle having line eof as the diameter and line oh as the radius.

In each of the above-described oval curves of FIGS. 1 and 2, the longest dimension thereacross coincides with the major axis of at least a portion of the elliptical curve. Although this is a preferred embodiment of the geometrical shape of a heart valve body, the longest dimension across the oval curve does not have to be coextensive with any particular geometrically defined line such as an axis of an ellipse or a diameter of a circle.

As used herein throughout this patent specification, "oval" refers to a curve having significantly different maximum dimensions thereacross at right angles to each other where one of the maximum dimensions is the longest dimension across the curve. The ratio of the shorter maximum dimension to the longer maximum dimension desirably is in the range of about 0.4 to 0.9. The curve desirably lies in a common plane, and preferably is everywhere concave inwardly.

For ease of layout and manufacture, it is desired that the heart valve annular bodies of the present invention have exterior peripheries defining oval curves that are symmetrical about either or both of the shorter or longer maximum dimensions as represented by lines cod and aob in FIG. 1. For example, the curve of FIG. 1 is symmetrical about the line cod, and the curve defined by the periphery p of the valve body of FIG. 6 is symmetrical about both its major and minor axes. The curves defined by valve bodies employed in the invention, however, may be egg-shaped as in FIG. 17 or kidney-shaped as in FIG. 19. An egg-shaped plane curved exhibits substantial symmetry about the longer maximum dimension as in FIG. 17. The kidney-shaped curve exhibits symmetry about neither the longer nor the shorter maximum dimension thereacross as in FIG. 19.

Each of the figures thus described is "oval" in that the figure is characterized by having significantly different maximum dimensions thereacross at right angles to one another, one of the maximum dimensions being the longest dimension of the two.

Description of FIGS. 3-5

FIG. 3 illustrates an upstream view of an oval heart valve 14 of the present invention. The oval heart valve 14 includes an annular valve body 14.1 having an exterior periphery similar to that of curve 10 in FIG. 1 in that the periphery comprises sections of two elliptical curves having a common major axis aob. Line oc represents a portion of the minor axis of the upper ellipse section acb and line od represents a portion of the minor axis of the lower ellipse section adb. The periphery of the valve body 14.1 is symmetrical about the line cod, but is asymmetrical about the line aob. The annular valve body 14.1 is of sufficient thickness which provides strength and rigidity, and includes an inner wall 14.2 which for the most part diverges outwardly at both sides of the body to provide the body with generally bell-shaped inflow and outflow sides 14.3 and 14.4 respectively as illustrated in FIG. 4. The inner wall of the annular valve body 14.1 defines the periphery of a blood flow passage 14.5 through the valve. The periphery of the blood flow pasage 14.5 desirably is oval and substantially similar, in a geometric sense, to the exterior periphery p of the valve body illustrated in FIG. 3. In a geometric sense, similar defines configurations that are of substantially the same shape but are of different sizes. The valve 14 includes a flow regulator for regulating the flow of blood through the passage 14.5 and includes a rigid occluder 16 as illustrated in FIG. 5 having the geometrical form of a flat plate which has an oval periphery "r". Pivots are carried by the valve body 14.1 for guiding the occluder 16 pivotally mounted in the flow passage between closed, occluding, and open, non-occluding positions.

FIG. 4, which illustrates a cross-sectional view taken along line 4—4 of FIG. 3, shows the open position of the occluder 16 as illustrated in solid lines and the closed position of the occluder 16 as illustrated in phantom lines. The pivot axis of the valve body 14.1 about which the occluder 16 pivots is designated as 14.6 in FIG. 3, and lies along the major axis of the valve body periphery. As illustrated in FIG. 4, the portions 14.7 of the interior wall of the valve body that are adjacent to the pivot axis 14.6 and inwardly concave from the inflow side 14.3 to the outflow side 14.4 to form sockets for retaining the occluder. The transition from the concave configuration of the sockets to the rounded, bell-shaped configuration shown in cross-section in FIG. 4 occurs smoothly along arcuate ridges 14.8 and 14.9.

FIG. 5, which is a cut plan view of the occluder 16 having a FIG. 5A side and a FIG. 5B side, shows a generally oval shape which is substantially similar in geometric shape to the blood flow passage 14.5 and to the periphery p of the valve body 14.1 The common major axis of the ellipse sections defining the periphery r of the occluder 16 is designated 16.1. The periphery of the occluder 16 can be notched at points spaced from the major axis. One such single concave notch configuration is illustrated at 16.2 in the A side of FIG. 5A. The notch 16.2 provides the occluder periphery at its point of intersection with the major axis 16.1 with a more sharply rounded portion 16.3. Another such double concave notch configuration is illustrated in the B side of FIG. 5B where notches 16.4 and 16.5 are spaced on both sides of the point of intersection of the occluder periphery with the major axis 16.1 thereby similarly providing the periphery with a sharply rounded portion 16.6. It will be understood that the configurations shown on the A and B sides of FIG. 5 are alternative configurations. The more sharply rounded peripheral portions of an occluder desirably are identical on both sides. The more sharply rounded peripheral portions designated 16.3 and 16.6 of the A and B sides of FIG. 5, respectively, are shaped to be received closely within the sockets defined by the concave portions 14.7 of the interior walls 14.2 of the valve body 14.1. The sockets prevent the occluder 16 from escaping from the valve body 14.1, but permit upstream and downstream translation of the occluder. The notches in the occluder periphery r provide relief for the arcuate ridges 14.8 and 14.9 thus permitting the occluder to translate between the upstream and downstream positions.

Pivot-closed pivots 15 and 15.1 in the form of small opposed projections protrude slightly inward of the blood flow passage 14.5 on each side of the periphery adjacent the inflow side 14.3 of the valve. The pivots 15 and 15.1 are mirror images of each other, and hence, only pivot 15 as also illustrated in FIG. 4 is described. Pivot 15 includes a closed position stop surface 15.2 in a plane parallel to the plane of the valve body 14.1 and facing the outflow side 14.4 of the valve 14, and also an open position stop surface 15.3 oriented at an oblique angle of 70° by way of example and for purposes of illustration only to the surface 15.2. The juncture of the surfaces 15.2 and 15.3 provides a rounded pivot edge 15.4. The pivots 15 and 15.1 are aligned with one another so that the edge 15.4 is in line with the opposed pivot edge of the other pivot as illustrated in FIG. 3. Pivot-open pivots 15.5 and 15.6 in the form of small opposed projections protrude slightly inward from the inner periphery of the valve body 14.1 adjacent to the outflow side 14.4 thereof. The pivots 15.5 and 15.6 are mirror images of each other, and hence, only the pivot 15.5 is described. The pivot 15.5 includes a closed position stop surface 15.7 in a plane parallel to the plane of the valve body 14.1 and facing the inflow side 14.3, and an open position stop surface 15.8 oriented at an oblique angle to the closed pivot stop surface 15.7. The open position stop surface 15.8 is generally parallel to the open position stop surface 15.3 of the pivot closed pivot 15. The juncture of the surfaces 15.7 and 15.8 provides a rounded pivot edge 15.9 that is generally parallel to the pivot edge 15.4 of the pivot closed pivot 15. The distance between the closed position stop surfaces 15.2 and 15.7 measured in a direction normal to the plane of the valve is slightly greater than the thickness of the occluder 16. The valve body 14.1 is made of a rigid, biologically acceptable material such as titanium, stainless steel, pyrolitic carbon, sapphire or ceramic. The rigid occluder 16 desirably is made of a strong but lightweight, biologically compatible material such as pyrolitic carbon produced by Carbomedics, Inc., sapphire or ceramic. The valve body 14.1 and the associated structure for carrying the occluder 16 desirably is manufactured as an integral part. The rigid occluder 16 is separately manufactured and is incorporated into the valve body 14.1 by a process involving very slightly deforming the valve body 14.1 to properly receive the occluder 16. In the event the valve body 14.1 is formed of a metal such as titanium or stainless steel, the valve body 14.1 can be resiliently deformed to receive the occluder 16.

Operation of FIGS. 3-5

The occluder 16 of FIGS. 3-5 is mounted in the valve body 14.1 with the more sharply rounded peripheral portions of the occluder 16 received within the inwardly concave socket portions 14.7 of the valve body 14.1 so that the occluder 16 can pivot easily between the open and closed positions as illustrated in FIG. 4. When the occluder 16 is in the closed position as illustrated in phantom lines in FIG. 4, upstream pressure on the occluder 16 causes the occluder 16 to physically move toward the outflow side 14.4 of the valve body 14.1 a short distance. Upstream pressure between the downstream-facing surface of the occluder 16, the disc stop surface 15.7 and pivot edge 15.9 causes the occluder 16 to pivot and slide along with pivot edge 15.9 into the open position as illustrated in solid lines in FIG. 4 wherein the flat walls of the occluder 16 come into surface contact with the open position stop surfaces 15.3 and 15.8 of the pivots 15 and 15.5 respectively. The latter surfaces are oriented with respect to one another to permit the occluder, in its open position, to assume an angle of about 70° with respect to the plane of the valve body 14.1. The sharply rounded peripheral portions of the occluder 16 are captured within the concave socket portions 14.7 of the valve body 14.1 come into sliding contact with the socket walls adjacent to the ridge 14.9 as the occluder 16 pivots into the open position and thus being prevented from escaping downstream of the valve body 14.1. As the downstream pressure begins to exceed the upstream pressure, the occluder 16 is urged in a generally upstream direction until the more sharply rounded peripheral portions of the occluder 16 come into contact with the concave socket portions 14.7 of the valve body 14.1 adjacent to the ridge 14.8, whereupon the occluder is pivoted about the pivot edge 15.4 in a pivoting, sliding motion into the closed position where the flat walls of the occluder 16 come into contact with the closed position stop surface 15.2. The stop surface 15.2 halts further pivoting movement of the occluder 16. The valve body 14.1 can be provided with an additional pivot stop projection 17 protruding slightly inward of the inner periphery of the valve body 14.1 approximately midway between the pivots 15 and 15.1. The projection 17 includes a downstream-facing stop surface 17.1 positioned which engages the occluder 16 when moving into the closed position as illustrated in FIG. 4. The exterior periphery of the valve body 14.1 is provided with spaced, outwardly extending flanges, 18 and 18.1 adjacent the inflow and outflow sides 14.3 and 14.4 respectively where the flanges define a groove about the periphery of the valve body 14.1 for reception of a surgical suturing ring 18.2. The surgical suturing ring, illustrated in phantom lines in FIGS. 3 and 4, is ties, cemented or otherwise held to the exterior periphery of the valve body 14.1. The suturing ring must be tightly affixed to the valve body 14.1 to prevent the valve body 14.1 and suturing ring 18.2 from becoming separated.

Description of FIGS. 6-9

FIGS. 6-9 illustrate another embodiment of an oval heart valve 20 of the present invention. The oval heart valve 20 includes an annular valve body 20.1 having an exterior periphery p which is substantially elliptical in shape. The inner periphery 20.2 of the valve body 20.1 defines a blood flow passage 20.5 that is substantially geometrically similar to the elliptical periphery p. The valve body 20.1 has generally bell-shaped inflow and outflow sides 20.3 and 20.4. Inwardly extending projections defining pivot-closed pivots 21 and 21.1, and pivot-open pivots 21.2 and 21.3 extend inwardly from the valve body 20.1. The pivot open and pivot closed pivots 21 and 21.2 each are provided with closed position stop surfaces 21.4 and 21.5, open position stop surfaces 21.6 and 21.7, and rounded pivot edges 21.8 and 21.9 defined by the respective junctures of the surfaces 21.4 and 21.6, and 21.5 and 21.7 respectively. The major axis 22 of the elliptical valve body is illustrated in FIG. 6. The pivot axis 22.1 is defined by the junctures of the pivot open pivots and pivot closed pivots, and is parallel to but spaced from the major axis 22 in the plane of the valve body 20.1. The internal periphery of the valve body 20.1 adjacent the pivot open and pivot closed pivots is contoured to provide inwardly concave sockets wherein the concave surfaces of the sockets merge into bell-shaped surfaces in the inner valve body periphery along arcuate ridges similar in structure to FIGS. 3 and 4.

FIG. 7 is a top view of the rigid occluder 24 for the valve of FIGS. 6 and 8. The flat, plate-like occluder 24 is substantially similar in geometric shape to the inner periphery 20.2 of the valve body 20.1. The occluder 24 is provided with notches 24.1 and 24.2 in the vicinity of the intersection of the major axis 24.3 with the occluder periphery, the notches providing the occluder with opposed, more sharply rounded peripheral portions 24.4, 24.5 which are received and held in the concave sockets of the valve body.

FIG. 8 which is a cross-sectional view taken along line 8—8 of FIG. 6, shows the occluder 24 in the open position in solid lines and in the closed position in phantom lines, the occluder 24 being movable in a pivoting, sliding fashion. The valve body 20.1 can be provided with a pivot stop projection 20.6 having a downstream-facing stop surface 20.7 adapted to abut and support the edge of the occluder when the latter is in its closed position.

Operation of FIGS. 6–9

Differences between the valves of FIGS. 3–5 and FIGS. 6–8 are the exterior peripheral shapes of the valve bodies and also the axes about which the respective occluders pivot. With the occluder in the closed position, the pivot axis of the valve body defined by the pivot edges 21.8 and 21.9 divide the upstream-facing area of the occluder into two portions of differing areas where the larger portion is nearer the pivot stop projection 20.6. In this instance, a greater force is imposed on the larger area portion of the occluder causing the occluder to pivot into the open position. In the valve 20 of FIGS. 6–8, the pivot axis 22.1 of the valve body 20.1 is spaced in the plane of the body away from the major axis 22, and the pivot axis of the occluder about which the occluder 24 of FIG. 7 initially begins to pivot is also spaced from the major axis 24.3.

Description of FIGS. 10–12

FIGS. 10–12 illustrate a further embodiment of an oval heart valve 26 of the present invention where FIG. 10 illustrates a view taken from the upstream side. The oval heart valve 26 includes a valve body 26.1 having a generally elliptical exterior periphery p. The inner periphery 26.2 of the valve body 26.1 defines a substantially elliptical blood flow passage 26.3 geometrically similar to the periphery p. The interior wall 26.2 of the valve body is flared outwardly at its edges as illustrated in FIG. 11 providing the valve body with smooth, bell-shaped inflow and outflow sides 26.4 and 26.5 respectively. The major and minor axes of the generally elliptical valve body are designated 26.6 and 26.7 respectively. A pivot post 26.8 extends inwardly of the valve body 26.1 along the minor axis 26.7 and adjacent to the outflow side 26.5, and terminates short of the major axis in a pivot stop surface 26.9 as illustrated in FIG. 11. The surface 26.9 is parallel to the major axis 26.6 and forms an oblique angle of 70° by way of example and for purposes of illustration with the plane of the valve body. The pivot post 26.8 includes a closed position stop surface 27 in a plane substantially parallel to the plane of the valve body and spaced from the mid-line of the body toward the outflow side 26.5. The surfaces 26.9 and 27 merge into a rounded pivot edge 27.1 parallel to the major axis 26.6 of the valve body. Arising from either side of the valve body and protruding inwardly of the flow passage are guide struts 27.2 and 27.3. The guide struts 27.2 and 27.3 are mirror images of each other, and hence, only the guide strut 27.2 is described in detail. The guide strut 27.2 arises from the inner periphery 26.2 of the valve body 26.1 adjacent to the inflow side at a position spaced from the major axis 26.6 in the direction of the pivot post 26.8. The guide strut 27.2 extends inwardly of the valve body periphery 26.2 a short distance, and then turns abruptly in the direction of the major axis 26.6. These portions of the guide strut 27.2 provide a downstream-facing, closed-position stop surface 27.4 which is parallel to the plane of the valve body, and also an open position stop surface 27.5 oriented at an angle of 70° by way of example and for purposes of illustration only to the surface 27.4. The surfaces 27.4 and 27.5 merge into a rounded pivot edge 27.6 parallel to the major axis 26.6 but spaced therefrom in the plane of the valve body facing towards the pivot post 26.8. At the major axis 26.6, the strut 27.2 turns in a downstream direction providing a guide portion 27.7. The portion 27.7 is perpendicular to the plane of the valve body 26.1 and has a generally circular cross-section. In the vicinity of the outflow side 26.5, the strut 27.2 bends again at an oblique angle, extending for a short distance 27.8 partly downstream and generally in the direction of the pivot post 26.8. The latter oblique portion 27.8 similarly has a generally circular cross-section but is of lesser diameter than the perpendicular guide portion 27.7.

FIG. 12, which is a plan view of an occluder 30 for the valve 26 of FIGS. 10–12, shows the rigid occluder 30 in the FIGS. 10–12 and having the geometrical form of a flat plate including a generally elliptical periphery r. The elliptical periphery is substantially geometrically similar to the shape of the blood flow passage 26.3. Dimensionally, the occluder 30 is very slightly smaller than the blood flow passage when the occluder 30 is in the closed position as illustrated in phantom lines in FIG. 11. The occluder 30 is provided with a pair of strut-receiving holes 30.1 and 30.2 through its thickness where the holes are desirably centered on the major axis 30.3 of the occluder 30 near the occluder periphery r in a position to loosely receive the perpendicular guide portion 27.7 of guide struts 27.2 and 27.3 when the occluder 30 is in the closed position. The diameter of the holes 30.1 and 30.2 is slightly larger than the diameter of the perpendicular guide portion 27.7 of the guide struts 27.2 and 27.3, and the inner surfaces 30.4 of the holes 30.1 and 30.2 are smoothly rounded as illustrated in FIG. 11. The periphery r of the oval occluder 30 of FIG. 12 is smoothly rounded. A separate closed position stop 27.9 extends inwardly of the flow passage 26.3 along the minor axis 26.7 of the valve body 26.1. The pivot post 26.8 lies in substantially the same plane as the stop surface 27.4 and the plane is spaced from the stop surface 27 of the pivot post 26.8 by a distance slightly greater than the thickness of the occluder 30. The closed position stop 27.9 including a stop surface 28 extends inwardly of the flow passage 26.3 a sufficient distance so that the stop surface 28 comes into contact with the upstream-facing flat surface of the occluder adjacent the periphery r when the occluder is in the closed position.

Operation of FIGS. 10–12

In operation, the varying blood pressure differentials across the valve produced by the beating of the human heart cause the occluder to pivot between its open and closed positions shown respectively in solid and in phantom lines in FIG. 11. When the occluder 30 is initially in the closed position, an increase of blood pressure upstream of the valve 26 causes the occluder 30 to lift away from the supportive surfaces 27.4 and 28 in a downstream direction whereupon the occluder 30 comes into contact with stop surface 27 on the pivot post 26.8. The occluder 30 then begins to pivot about the pivot edge 27.1 and concurrently moves downstream as permitted by the guide struts 27.2 and 27.3 where the inner peripheries of the occluder 30 holes bear against the confronting surfaces of the guide struts 27.2 and 27.3. The flattened surface of the occluder 30 coenacts with the pivot edge 27.1 in a pivoting, sliding manner. The reduced diameter of the oblique portion 27.8 of the guide strut 27.2 further provides downstream movement of the occluder 30. The pivoting, sliding movement of the occluder 30 continues until the flat surface comes into contact with the pivot open stop surfaces 26.9 and 27.5 as illustrated in FIG. 11. The surfaces 26.9 and 27.5 lie in planes spaced from one another by a distance approximating the thickness of the occluder, and each surface is at an angle of 70° by way of example and for purposes of illustration only to the plane of the valve body. Thus, in the open position, the occluder 30 is restrained from further downstream movement by the oblique portion 27.8 of the guide strut 27.2, and is restrained from further pivoting movement by the guide surfaces 26.9 and 27.5.

As the pressure downstream of the valve 26 begins to exceed the upstream pressure, the occluder 30 initially moves upstream a short distance afforded by the difference in diameters of the occluder hole 30.4 and the oblique portion 27.8 of the guide strut 27.2 but without contact between 27.8 and 30.1. Instead the periphery r should engage the inner wall of valve body 26.1 in the region of attachment of guide struts 27.2 and 27.3. Guided by the guide struts 27.2 and 27.3, the occluder 30 begins pivoting about the edge 27.6 in a sliding, pivoting action where the occluder 30 thus returns to the closed position as illustrated in FIG. 11. As the occluder 30 reaches the closed position, the generally upstream-facing flat surface comes into contact with the stop surfaces 27.4 and 28.

Description of FIGS. 13–16

FIGS. 13–16 illustrate an additional embodiment of an oval heart valve 32 of the present invention where FIG. 13 is a plan view taken from the upstream side. The oval heart valve 32 includes a valve body 32.1 having a generally elliptical oval periphery p including a major axis 32.2 and a minor axis 32.3. The inner wall 32.4 of the valve body 32.1 defines a blood flow passage 32.5 therethrough which is oval and which is substantially geometrically symmetrical to the exterior periphery p. As in previous embodiments, the inner wall 32.4 of the valve body is flared outwardly at its edges to provide bell-shaped inflow and outflow sides 32.6 and 32.7 respectively. A generally T-shaped pivot post 32.8 arises from the inner periphery of the valve body 32.1 adjacent to the outflow side 32.7. The pivot post 32.8 includes a shank portion 32.9 which extends inwardly of the valve body along the minor axis 32.3, and terminates inwardly in a cross member 33 perpendicular to the shank and parallel to the major axis 32.2 of the valve body 32.1. The cross member 33 has a length which approximates one-half of the major diameter of the blood flow passage and is provided with an upstream-projecting lip 33.1 having a smooth, upstream-facing pivot edge 33.2. The shank 32.9 is also provided with a generally upstream-facing pivot-closed stop surface 33.3 where the surface tapers downstream slightly toward the center of the valve body 32.1. The pivot cross member 33 terminates inwardly of the blood flow passage in an open position stop surface 33.4 which is parallel to the major axis and is oriented at an oblique angle of 70° by way of example and for purposes of illustration only to the plane of the valve body. The pivot cross member 33 is spaced from the major axis in the direction of the shank 32.9.

Arising from the inner wall 32.4 of the valve body 32.1 at the inflow side 32.6 of the valve are opposed pivot closed projections 33.5 and 33.6. These pivots are mirror images of one another, and hence, only pivot 33.5 is described in detail.

The pivot 33.5 extends inwardly a short distance from the periphery of the valve body 32.1, and includes a downstream-facing closed position stop surface 33.7 as illustrated in FIG. 14 and an open position stop surface 33.8 which lies at an oblique angle of about 70° by way of example and for purposes of illustration only to the plane of the valve body 32.1. The surfaces 33.8 and 33.7 merge into a smoothly rounded pivot edge 33.9. The pivot edge 33.9 of each of the pivots 33.5 and 33.6 are aligned with one another and are spaced from the major axis 32.2 of the valve body 32.1 in the direction of the pivot post shank 32.9. A pivot closed stop 34 having a downstream-facing closed position stop surface 34.1 arises from the inner surface of the valve body 32.1 opposed to the pivot post 32.8 and lies in the same plane as the surface 33.7. The surfaces 33.7 and 34.1 define a plane spaced in an upstream direction from the mid-line of the valve body.

The rigid occluder 36 includes a generally oval periphery r, and an upstream-facing surface 36.1 which is substantially flat. The generally downstream-facing surface 36.2 of the occluder 36 is provided with a wedge-shaped depression 36.3 forming a gently rounded, elongated pivot socket 36.4. The pivot socket is parallel to but spaced from the major axis 36.5 of the occluder 36. The length of the socket 36.4 is sufficient to receive the elongated lip 33.1 of the pivot post cross member 33 as illustrated in FIG. 14. The wall 36.6 of the occluder 36 defining one side of the elongated socket 36.4 is at an angle of 90° by way of example and for purposes of illustration to the plane of the occluder 36 which thereby retains the elongated lip 33.1 of the pivot cross member 33 within the socket 36.4 having edges 36.8 when the occluder 36 is in the open position as illustrated in solid lines in FIG. 14. The generally downstream-facing surface 36.7 of the occluder 36 adjacent the wall 36.6 tapers gently toward the periphery of the occluder, and is configured to closely confront or engage the stop surface 33.3 of the pivot post when the occluder is in the closed position. Other portions of the downstream-facing surface of the occluder merge gently into the periphery thereof and into side walls 36.8 of the wedge-shaped depression 36.3 thus eliminating sharp angles and corners.

Operations of FIGS. 13–16

The occluder 36 is illustrated in the closed position in phantom lines in FIG. 14. As the pressure of blood upstream of the valve 32 increases, the occluder 36 moves in a downstream direction until the socket 36.4 engages the elongated lip 33.1 of the pivot post whereupon the occluder 36 pivots into the open position as illustrated in solid lines in FIG. 14. The distance as measured along line 14—14 of FIG. 13 between the pivot edge 33.9 and the pivot edge defined by the lip 33.1 is less than the maximum thickness of the occluder 36 adjacent the socket 36.4, and hence, the occluder 36 does not escape in a downstream direction from the valve body 32.1. When the occluder 36 has reached the open position, the generally upstream-facing surface adjacent the periphery comes into contact with the open position stop surfaces 33.8 and the open position stop surface 33.4 engages the confronting surface of the occluder 36. The open position stop surfaces 33.8 and 33.4 are oriented so as to permit the occluder 36 to pivot into a maximum open position in which its upstream-facing surface forms an angle of substantially 70° with the plane of the valve body.

As the blood pressure downstream of the valve 32 increases, the occluder 36 is transported upstream until the peripheral edges make sliding contact with the peripheral edges of the inner wall 32.4 of the valve body, and thereafter, the occluder 36 pivots about the pivot edges 33.9 of the pivot closed pivots 33.5 and 33.6 in a pivoting, sliding manner. The length of the chord defined by the pivot edges 33.9 is less than the distance across the occluder measured along the major axis 36.5 and, hence, the occluder 36 does not escape from the valve body in an upstream direction during closing. As the occluder 36 reaches the closed position, further pivoting movement is stopped by contact of the upstream-facing surface 36.1 of the occluder 36 with the stop surfaces 33.7 and 34.1.

Description of FIGS. 17 and 18

The oval heart valve 40 includes a valve body 40.1 having a generally egg-shaped periphery p. The longest dimension across the periphery is measured along line 40.2, and the maximum dimension at right angles to the longest dimension is taken along line 40.3. The periphery of the valve body is substantially symmetrical with respect to the line 40.2, but is asymmetrical with respect to the line 40.3. The inner wall 40.4 of the valve defines a blood flow passage 40.5 that is substantially geometrically similar to the exterior periphery p of the valve body.

The rigid occluder 44 is in position within the blood flow passage 40.5 as illustrated from the upstream side of the valve 40 and pivots downstream into at least a partially open position similar to FIGS. 3, 6, 10 and 13. The valve body 40.1 is provided with inwardly extending projections defining pivot closed pivots 40.6 and 40.7, and pivot open pivots 40.8 and 40.9 which are substantially identical to the pivot open pivots and pivot closed pivots described with reference to the embodiment of FIGS. 6-8. The pivot axis 41 defined by the pivot open and pivot closed pivots is parallel to but is spaced from the line 40.2. The internal periphery of the valve body in the vicinity of the pivot open and pivot closed pivots 40.6 through 40.9 is contoured providing inwardly concave sockets which are identical to the sockets described with reference to the embodiment of FIGS. 6-8. The inner wall of the valve body is also provided with a closed position stop 41.1 which is identical to the pivot stop 20.6 illustrated in FIGS. 6-8.

The rigid occluder 44 includes a generally egg-shaped exterior periphery r that is substantially similar to the periphery of the blood flow passage 40.5 through the valve body 40.1. The periphery r of the occluder 44 is symmetrical about the line 44.1, the latter line being coincident with the line 40.2 of FIG. 17 when the occluder is in the closed position. The occluder 44 is provided with notches 44.2, 44.3 and 44.4, 44.5 providing the occluders between the notches with more sharply rounded peripheral portions 44.6 and 44.7 which are received and held in the above-described concave sockets of the valve body 40.1 in the manner identical to that of the embodiment described with reference to FIGS. 6-8. The pivot axis 44.8 of the occluder defined by the more sharply rounded portions 44.6 and 44.7 of the occlunder periphery is parallel to but spaced from the line of symmetry 44.1.

Operations of FIGS. 17 and 18

The embodiment delineated in FIGS. 17 and 18 is substantially identical to the embodiment delineated in FIGS. 6-8 except that the exterior periphery p of the valve body, the blood flow passage 40.5, and the periphery r of the occluder 44 are egg-shaped rather than elliptical where the periphery p of the valve body 40.1 has but a single axis of symmetry which is parallel to the pivot axis defined by the inflow and outflow pivots. The operation of the valve 40 of FIGS. 17 and 18 is identical to that of the valve of FIGS. 6-8 and no further operational description of the valve of FIGS. 17-18 is required. The occluder 44 is not symmetrical about any line in its plane perpendicular to the pivot axis 44.8. The closed position stop for such valves, designated 20.6, 27.9 and 34 in FIGS. 6, 10 and 13, respectively, arising from the inner valve body wall at or near the point of intersection of the minor axis for each such valve, is oriented to make contact with the valve along the minor axis of the latter thereby generally equalizing the stresses placed on each of the sockets and pivot stops on either side of the valve. In the valve shown in FIG. 17, however, the occluder is not symmetrical about a line perpendicular to its pivot axis. As a result, when the occluder pivots to its closed position into contact with the closed position stop 41.1, the unbalanced nature of the occluder may cause it to tilt slightly into the flow passage on either side of the stop 41.1 thereby providing unequal stresses on the pivot open and pivot closed pivots and upon the sockets. This phenomenon may be checked by increasing the width of the closed position stop 41.1 so that the latter contacts the occluder 44 along a significant portion of the peripheral length of the occluder. More desirably, however, the center of gravity of the occluder is measured, and the closed position stop 41.1 is positioned to engage that portion of the occluder periphery lying on a line drawn through the center of gravity and at right angles to the pivot axis 44.8.

Description of FIGS. 19 and 20

The oval heart valve includes a valve body 46.1 having a generally kidney-shaped periphery p that has no axis of symmetry. The inner periphery 46.2 of the valve body defines a blood flow passage 46.3 that is substantially geometrically similar to the periphery p. The valve body is provided with pivot closed pivots 46.4 and 46.5, and pivot open pivots 46.6 and 46.7, respectively, projecting radially inward from opposing portions of the inner valve body periphery. The inner wall of the valve body is provided with sockets in the vicinity of the pivots as described in the previous embodiments. The pivot axis 46.8 defined by the pivots is illustrated in FIG. 19 where the pivot axis divides the blood flow passage 46.3 into two unequal flow areas of which the lower area illustrated in FIG. 19 is larger. The valve body 46.1 is also provided with a closed position stop 46.9 having a downstreamfacing stop surface. As thus described, the pivot open and pivot closed pivots 46.4-46.7, the sockets, and the closed position stop 46.9 are substantially identical to the pivots, sockets and stops described above with reference to the valve of FIGS. 6-8. Accordingly, further detailed description of these elements is not set forth.

The rigid occluder 50 for the valve of FIG. 19 is illustrated in FIG. 20 and includes an oval periphery r of the occluder 50 which is generally kidney-shaped and substantially geometrically similar to the blood flow passage 46.3 of the valve body. Spaced notches 50.1, 50.2 and 50.3, 50.4 are provided on opposing edges of the occluder periphery as illustrated in FIG. 20 providing the periphery with opposed, more sharply rounded portions 50.5 and 50.6. The sharply rounded portions 50.5 and 50.6 define an occluder pivot axis 50.7. As in the previously described embodiments, the more sharply rounded peripheral portions 50.5 and 50.6 are received within sockets formed in the inner wall of the valve body. The operation of the valve 46 is substantially identical to that of the valve of FIG. 6–8, and hence, is not described in detail.

The periphery p of the valve body 46.1 of FIG. 19 is most nearly flat at its top, and the pivots 46.4–46.7 are located as to position the pivot axis 46.8 generally parallel with the top portion of the valve body periphery. Note, however, that the longest distance across the periphery p is measured along line 47 which is not parallel to the pivot axis 46.8. Similarly, the maximum distance across the periphery perpendicular to the line 47 is measured along the line designated 47.1 which is at an oblique angle to the pivot axis 46.8. The longest dimension across the periphery of the occluder excluding the notches is measured along line 50.8, and the maximum dimension taken perpendicular to the line 50.8 is measured along line 50.9. Lines 50.8 and 50.9 are at an oblique angle to the pivot axis 50.7.

As illustrated in FIG. 19, the pivot axis 46.8 divides the blood flow passage 46.3 into a generally small, upper area and a large, lower area. The large difference in these areas causes the occluder to pivot open and closed more forcefully under cycling blood pressures, and further provides the valve with a large and substantially unobstructed blood flow passage portion defined by the upstream surface of the occluder and the portion of the inner valve body periphery below the pivot axis 46.8. As explained in detail in the embodiment of FIG. 17, the closed position stop 46.9 is positioned along the inner periphery of the valve 46 along the line perpendicular to the pivot axis 46.8 and passing through the center of gravity of the occluder.

Various modifications can be made to the present invention without departing from the apparent scope thereof.

Having thus described the present invention, what is claimed is:

1. Heart valve comprising:
a. valve body including a non-circular exterior periphery and an inner wall defining a blood flow passage having a periphery substantially geometrically similar to said exterior periphery;
b. occluder including a periphery substantially geometrically similar to said blood flow passage; and
c. means integral with said valve body supporting and guiding said occluder in said blood flow passage between a non-occluding and occluding position including bell-shaped inflow and outflow sides, pivot axis extending across one of the maximum dimensions of said non-circular body, opposed inwardly concave socket portions in said valve body at said pivot axis, and arcurate ridges on each side of said inwardly concave portions.

2. The heart valve of claim 1 wherein said valve body comprises opposed pivot closed pivots projecting inwardly on each side of said exterior periphery adjacent said inflow side and including a closed position stop surface, a pivot edge, and an open position stop surface and opposed pivot open pivots projecting inward on each side of said exterior periphery adjacent said outflow side and including a closed position stop surface, a pivot edge, and an open position stop surface.

3. The heart valve of claim 2 wherein said occluder comprises a rigid body, common major axis across said exterior periphery and a sharply rounded portion about a concave notch at each end of said major axis whereby said sharply rounded portion defines a pivot axis of said occluder.

4. The heart valve of claim 2 wherein said occluder comprises a rigid body, common major axis across said exterior, and a sharply rounded portion about concave notches at each end of said major axis whereby said sharply rounded position defines a pivot axis of said occluder.

5. The heart valve of claim 4 wherein said valve body comprises a pivot stop projection extending inwardly on said inflow side and including a downstream-facing stop surface.

6. The heart valve of claim 1 comprising spaced flanges extending outwardly from said valve body whereby a surgical suturing ring secures between said flanges.

7. The heart valve of claim 4 wherein said exterior periphery of said valve body includes maximum dimensions at right angles to each other, one of said maximum dimensions being the greater of the two and said pivot means including pivot ends defining a pivot axis whereby said pivot axis is parallel to said greater dimension across said valve body.

8. The heart valve of claim 7 wherein said pivot axis is substantially coextensive with said greater dimension across said valve body.

9. The heart valve of claim 7 wherein said pivot axis is substantially parallel to but spaced from said greater dimension across said valve body.

10. The heart valve of claim 7 wherein the ratio of said maximum dimensions does not exceed 0.9.

11. The heart valve of claim 1 wherein said non-circular periphery is oval.

12. The heart valve of claim 1 wherein said non-circular periphery is elliptical.

13. Heart valve comprising:
a. valve body including a non-circular exterior periphery, an inner wall defining a blood flow passage through said valve body, and pair of opposed guide struts projecting outwardly from an inflow side of said valve body and including guide portions extending within said blood flow passage;
b. flat, rigid occluder substantially geometrically similar to said blood flow passage and including pair of opposed spaced holes substantially along a major axis of said occluder which receive said respective guide portions of said guide struts;
c. pivot means extending outwardly from said outflow side of said valve body; and
d. restraining means extending inwardly from said inflow side of said valve body whereby said pivoting means engages with said occluder thereby providing a pivot surface during pivoting of said occluder into a non-occluding position in response to a downstream blood pressure drop across said heart valve.

14. The heart valve of claim 13 wherein each of said guide struts comprise in order from said valve body of an open position stop surface, a rounded pivot edge, a downstream facing closed position stop surface, a perpendicular guide portion and an oblique guide portion.

15. The heart valve of claim 14 wherein said pivot means comprises in order from said valve body a closed position stop surface, a rounded pivot edge, and a pivot stop surface.

16. The heart valve of claim 14 wherein said restraining means comprises a closed position stop including a stop surface.

17. Heart valve comprising:
a. valve body including a non-circular exterior periphery and non-circular interior blood flow passage substantially geometrically similar to said exterior periphery of said valve body;
b. flat rigid occluder including a pivot socket on a downstream-facing surface and receivable in said blood flow passage;
c. pivot post means extending radially inward of said blood flow passage on an outflow side of said valve body and including a substantially upstream facing pivot surface pivotally received in said pivot socket;
d. opposed pivot closed projections extending inward of said blood flow passage on an inflow side of said valve body; and
e. restraining means extending inwardly on said outflow side of said valve body whereby said occluder pivots in said blood flow passage between occluding and nonoccluding position.

18. The heart valve of claim 17 wherein said pivot post means comprises a T-shaped pivot post, a shank portion, and a cross member including an upstream projecting lip, an upstream facing pivot closed stop surface, an upstream facing pivot edge, and an open position stop surface.

19. The heart valve of claim 17 wherein said restraining means comprises a pivot closed stop including a downstream facing closed position stop surface.

20. The heart valve of claim 17 wherein said occluder includes parallel upstream and downstream facing surfaces, a wedge shaped depression in said downstream facing surface, said pivot socket being rounded, depression and elongated, and said major axis coinciding with said elongated depression.

* * * * *